United States Patent
Florio

(10) Patent No.: US 6,516,225 B1
(45) Date of Patent: Feb. 4, 2003

(54) SYSTEM AND METHOD FOR DISTINGUISHING ELECTRICAL EVENTS ORIGINATING IN THE ATRIA FROM FAR-FIELD ELECTRICAL EVENTS ORIGINATING IN THE VENTRICLES AS DETECTED BY AN IMPLANTABLE MEDICAL DEVICE

(75) Inventor: Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 41 days.

(21) Appl. No.: 09/662,440

(22) Filed: Sep. 15, 2000

Related U.S. Application Data

(60) Provisional application No. 60/173,417, filed on Dec. 28, 1999, and provisional application No. 60/173,341, filed on Dec. 28, 1999.

(51) Int. Cl.[7] .............................................. A61N 1/368
(52) U.S. Cl. ......................................... 607/9; 600/510
(58) Field of Search ....................... 607/4–27; 600/509, 600/510

(56) References Cited

U.S. PATENT DOCUMENTS

| | | | |
|---|---|---|---|
| 5,342,405 A | 8/1994 | Duncan | |
| 5,466,254 A | 11/1995 | Helland | |
| 5,601,613 A | 2/1997 | Florio et al. | |
| 5,620,471 A | 4/1997 | Duncan | |
| 5,788,717 A | 8/1998 | Mann et al. | |
| 5,991,656 A | 11/1999 | Olson et al. | ................... 607/6 |
| 6,029,087 A | 2/2000 | Wohlgemuth | |
| 6,052,620 A | 4/2000 | Gillberg et al. | ................ 607/4 |

*Primary Examiner*—Scott M. Getzow

(57) ABSTRACT

The system and method discriminates P-waves or other electrical events originating in the atria from R-waves or other electrical events originating in the ventricles. In one example, far-field R-waves in the atria are distinguished from true P-waves using both a post-ventricular atrial blanking (PVAB) interval and a separate pre-ventricular blanking interval (pre-VAB) interval. Insofar as the pre-VAB interval is concerned, upon detection of a P-wave in the atria, the implantable medical device begins tracking a pre-VAB interval. If an R-wave is then detected in the ventricles during the pre-VAB interval, the P-wave is rejected as being a far-field R-wave. A PVAB interval may also be employed to filter out any P-waves detected in the atria immediately following detection of an R-wave in the ventricles. In another example, far-field R-waves are distinguished from true P-waves using template matching. P-waves detected in the atria are compared against a template representative of true P-waves. If the P-wave substantially matches the template, the P-wave is deemed to be a true P-wave; otherwise, the P-wave is rejected as being a far-field R-wave or other anomalous electrical event. In both examples, the techniques are applicable to other types of electrical events detected within the heart besides P-waves and R-waves, such as electrical events occurring during fibrillation or flutter when discrete P-waves and R-waves may not be detectable.

15 Claims, 5 Drawing Sheets

SYSTEM AND METHOD FOR DISTINGUISHING ELECTRICAL EVENTS ORIGINATING IN THE ATRIA FROM FAR-FIELD ELECTRICAL EVENTS ORIGINATING IN THE VENTRICLES AS DETECTED BY AN IMPLANTABLE MEDICAL DEVICE

CROSS-REFERENCE TO RELATED APPLICATIONS

This application claims the benefit of U.S. Provisional Application No. 60/173,417, filed Dec. 28, 1999; and is related to copending U.S. Provisional No. 60/173,341, filed Dec. 28, 1999.

FIELD OF THE INVENTION

The invention generally relates to implantable medical devices, such as pacemakers or implantable cardioverter-defibrillators ("ICDs") and, in particular, to techniques for analyzing electrical events detected within the heart using an implantable medical device.

BACKGROUND OF THE INVENTION

A pacemaker is a medical device, typically implanted within a patient, which recognizes various dysrhythmias such as an abnormally slow heart rate (bradycardia) or an abnormally fast heart rate (tachycardia) and delivers electrical pacing pulses to the heart in an effort to remedy the dysrhythmias. An ICD is a device, also implantable into a patient, which additionally recognizes atrial fibrillation (AF) or ventricular fibrillation (VF) and delivers electrical shocks to terminate fibrillation.

Pacemakers and ICD's carefully monitor characteristics of the heart such as the heart rate to detect dysrhythmias, discriminate among different types of dysrhythmias, identify appropriate therapy, and determine when to administer the therapy. The heart rate, for example, is monitored by examining the electrical signals that are manifest concurrent with the depolarization or contraction of the myocardial tissue of the heart. The electrical signals are detected internally by sensing leads mounted within the heart and are referred to as internal electrocardiogram ("IEGM") signals. The normal contraction of atrial muscle tissue appears as a P-wave within the IEGM. A sequence of consecutive P-waves defines the atrial rate. The normal contraction of ventricular muscle tissue appears as an R-wave (sometimes referred to as the "QRS complex") within the IEGM. A sequence of consecutive R-waves defines the ventricular rate. If the heart is subject to flutter or fibrillation, P-waves and R-waves typically cannot be discerned within the IEGM. Hence, the pacemaker or ICD may need to rely on other characteristics of the IEGM to discriminate among different types of flutter and fibrillation, to identify optimal therapy, and to determine when to administer the therapy. Some state of the art pacemakers and ICD□s are capable of sensing electrical signals independently in the atria and in the ventricles. Hence, an atrial IEGM and a separate ventricular IEGM are detected. The atrial rate is determined based upon P-waves detected in the atrial IEGM. The ventricular rate is determined based upon R-waves detected within the ventricular IEGM.

Thus pacemakers and ICD's administer therapy to the heart, in part, based upon the detection of electrical characteristics of the heart such as P-waves, R-waves, atrial rate, ventricular rate, and the like. As one specific example, if the atrial and ventricular rates are both below a minimum acceptable heart rate threshold or if long gaps appear within the IEGM signals wherein no P-waves and R-waves are sensed, the cardiac pacing device thereby concludes that the patient is suffering from bradycardia and administers pacing pulses in an effort to increase the heart rate or to eliminate long gaps without heart beats. As another specific example, if the atrial and ventricular rates are well above a maximum expected heart rate, the cardiac pacing device concludes that the patient is suffering from a tachyarrhythmia and administers appropriate therapy such as, for example, overdrive pacing in an effort to lower the heart rate to within an acceptable range. If the atrial rate is found to be extremely high, but the ventricular rate is relatively normal, the cardiac pacing device concludes that the patient is suffering from atrial flutter or atrial fibrillation and administers a defibrillation pulse to the atria. If the ventricular rate is extremely fast and chaotic, the cardiac pacing device concludes that the patient is suffering from ventricular fibrillation and administers a defibrillation pulse directly to the ventricles. Details regarding techniques for discriminating between atrial and ventricular dysrhythmias or arrhythmias are provided in U.S. Pat. No. 5,620,471 to Duncan entitled "System and Method for Discriminating Between Atrial and Ventricular Arrhythmias and for Applying Cardiac Therapy Therefor", issued Apr. 15, 1997, which is incorporated by reference herein.

Reliable operation of pacemakers and ICD□s therefore necessitates that the device be capable of accurately detecting P-waves, R-waves or other electrical events originating within the heart. Insofar as P-waves are concerned, however, the aforementioned R-waves, though initially generated within the ventricles, propagate into the atria and may be detected therein as part of the atrial IEGM signal. It is therefore possible for the device, upon detecting an electrical pulse within the atria, to misidentify a far-field R-wave as being a P-wave. As a result, any functions performed by the pacemaker which require accurate determination of P-waves may not function as intended. For example, PVCs may be classified as P-R events so that the calculated atrial rate will be higher than the actual atrial rate, perhaps causing the device to erroneously conclude that the atria are subject to a tachyarrhythmia, which does not in fact exist, or classify a ventricular tachycardia as an atrial tachycardia. Alternatively, the overestimated atrial heart rate may cause the device to fail to detect a bradycardia, which does exist. As a result, inappropriate therapy may be administered. For an ICD, an erroneously high determination of the atrial rate may cause the ICD to incorrectly conclude that the heart is subject to atrial fibrillation, resulting in a potentially painful cardioversion pulse administered to the atrium.

Thus, it is necessary to properly distinguish P-waves or other electrical events originating in the atria from far-field R-waves or other events originating in the ventricles. Accordingly, most state-of-the-art pacemakers ignore any events detected within the atria during a predetermined period of time subsequent to the detection of an R-wave in the ventricles. This period of time is referred to as the post-ventricular atrial blanking (PVAB) interval or a post-ventricular atrial refractory period (PVARP). Briefly, upon the detection of an R-wave from a sensing electrode positioned within the ventricles, the pacemaker thereafter ignores any events detected from a sensing lead within the atria for a period of time (e.g. 225 ms.) under the assumption that any event detected during that period of time is actually a far-field R-wave.

The use of the PVAB interval presupposes that the R-wave will be detected in the ventricles before it appears as a far-field R-wave in the atria. This is not always the case. The inventors of the present invention have determined that circumstances can arise wherein a far-field R-wave is detected within the atria before it is detected within the ventricles. This may occur, for example, if an atrial sensing lead is positioned closer to the source of an R-wave than the ventricular sensing leads. Another circumstance wherein an R-wave may be detected within the atria without a preceding R-wave detection in the ventricles occurs if the threshold for R-wave detection in the ventricles is set too high, such that some R-waves are not detected at all within the ventricles. In any event, if the far-field R-wave is detected within the atria without an immediately preceding R-wave detection in the ventricles, the aforementioned PVAB interval is ineffective to filter out the far-field R-wave from the atrial IEGM. As a result, far-field R-waves are misclassified as P-waves resulting in incorrect determination of atrial rate, or other critical parameters, causing potentially erroneous therapy to be administered by the pacemaker. Although these problems have been described primarily with reference to the discrimination of P-waves from far-field R-waves, similar problems arise even in circumstances wherein P-waves and R-waves cannot be discerned within the IEGM, such as during flutter or fibrillation.

Accordingly, it would be highly desirable to provide an improved technique for discriminating P-waves or other electrical events originating within the atria from far-field R-waves or other electrical events originating within the ventricles, and it is to that end that aspects of the present invention are primarily directed.

SUMMARY OF THE INVENTION

In accordance with one aspect of the invention, a method is provided for discriminating between electrical events originating in the atria from electrical events originating in the ventricles using an implantable medical device employing a pre-ventricular blanking interval (pre-VAB). In accordance with the method, a determination is made as to whether an electrical event detected within one of the ventricles was detected within a predetermined pre-VAB interval following detection of an electrical event within one of the atria. If so, the electrical event of the atria is rejected as being a far-field ventricular electrical event or other non-atrial electrical event.

Within an exemplary embodiment, the electrical event of the atria is a P-wave and the electrical event of the ventricle is an R-wave. The implantable medical device determines whether the R-wave was detected within a predetermined pre-VAB interval following detection of the P-wave and, if so, the P-wave is rejected as being a far-field R-wave. The implantable medical device is also configured to determine whether the P-wave was detected within a predetermined PVAB interval following detection of an R-wave in the ventricles and, if so, the P-wave is likewise rejected as being a far-field R-wave. In this manner, a far-field R-wave within the atria is properly rejected regardless of whether it is sensed before or after the R-wave of the ventricle. Accordingly, problems associated with misclassification of far-field R-waves are reduced or avoided completely. In other embodiments, the electrical events within the atrial and ventricular IEGM signals represent other detectable events besides P-waves or R-waves, such as events detectable during flutter or fibrillation. Hence, the technique is not limited to processing atrial and ventricular IEGM signals in which P-waves and R-waves can be discerned but is applicable to other situations as well.

In accordance with another aspect of the invention, a method is provided for discriminating electrical events originating in the atria from other electrical events based upon template matching. In accordance with the method, an electrical event detected within the atrium is compared against a template representative of a true atrial event. If the detected event substantially matches the template, the event is deemed to be a true atrial event; otherwise the event is discarded as being a far-field ventricular event or other anomalous electrical event. Within an exemplary embodiment, the template is representative of the amplitude shape of a P-wave, and hence the method discriminates true P-waves from far-field R-waves. In other embodiments, the template is representative of other characteristics of a P-wave, such as its frequency characteristics, rather than its amplitude characteristics. In still other embodiments, the template is representative of other electrically detectable events, such as events occurring during flutter or fibrillation.

BRIEF DESCRIPTION OF THE DRAWINGS

Further features and advantages of the present invention may be more readily understood by reference to the following description taken in conjunction with the accompanying drawings, in which:

FIG. 5 is a graph illustrating an atrial event and a template representative of a true P-wave processed by the method of FIG. 4.

DETAILED DESCRIPTION OF THE INVENTION

With reference to the figures, preferred and exemplary embodiments of the invention will now be described. The embodiments will primarily be described with reference to an ICD capable of detecting separate atrial and ventricular IEGM signals and configured for discriminating between events appearing within the IEGM that originated within the atria and events appearing within the IEGM that originated elsewhere. Hence, the following description is not to be taken in a limiting sense but is made merely for the purpose of describing the general principles of the invention. The scope of the invention should be ascertained with reference to the issued claims. The following description includes the best mode presently contemplated for practicing the invention. In the description of the invention that follows, like numerals or reference designators will be used to refer to like parts or elements throughout.

Figure 1:
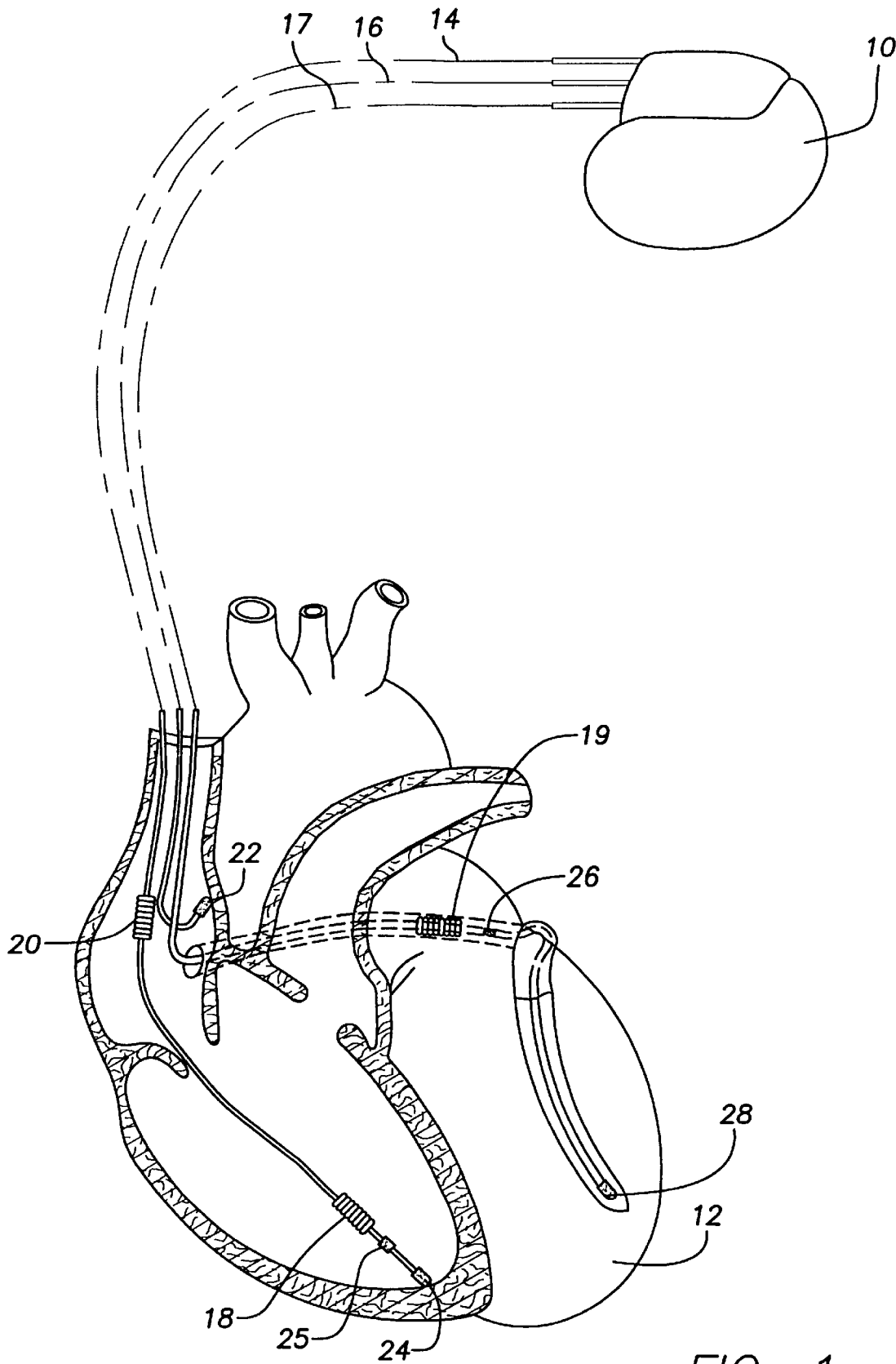
FIG. 1 is a diagram of an ICD connected to the heart of a patient.

FIG. 1 illustrates a multi-chamber implantable stimulation device 10 which is capable of treating both fast and slow arrhythmias with stimulation therapy, including cardioversion, defibrillation, and pacing stimulation. While a multi-chamber device is shown, this is for illustration purposes only, and one of skill in the art could readily eliminate or disable the appropriate circuitry to provide a single-chamber or dual-chamber stimulation device capable of treating one or two chambers with cardioversion, defibrillation and pacing stimulation.

To provide right atrial chamber pacing stimulation and sensing, the stimulation device 10 is shown in electrical communication with a patient's heart 12 by way of an implantable atrial lead 16 having an atrial tip electrode 22 and (optionally) an atrial ring electrode (not shown) which typically is implanted in the patient's atrial appendage.

The stimulation device 10 is also shown in electrical communication with the patient's heart 12 by way of an implantable ventricular lead 14 having, in this embodiment, a ventricular tip electrode 24, a ventricular ring electrode 25, a right ventricular (RV) coil electrode 18, and an SVC coil electrode 20. Typically, the ventricular lead 14 is transvenously inserted into the heart 12 so as to place the RV coil electrode 18 in the right ventricular apex, and the SVC coil electrode 20 in the superior vena cava. Accordingly, the ventricular lead 14 is capable of receiving cardiac signals, and delivering stimulation in the form of pacing and shock therapy to the right ventricle.

To sense left atrial and ventricular cardiac signals and to provide left chamber pacing therapy, the stimulation device 10 is coupled to the "coronary sinus" lead 17 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. For a complete description of a coronary sinus lead, see U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which patents are hereby incorporated herein by reference.

As shown, the sensing/pacing locations are right atrium (high septal wall), left atrium (distal coronary sinus), right ventricular apex and left ventricle (via a cardiac vein). In the exemplary embodiment, the ICD combines signals received from the atrial sensing locations into a single atrial IEGM signal and combines signals received from the ventricular sensing locations into a single ventricular IEGM signal. In other embodiments to be described below, the ICD processes the left and right IEGM signals separately.

Among other functions, the ICD analyzes the atrial and ventricular IEGM signals to determine whether an atrial or ventricular tachyarrhythmia is occurring and whether cardioversion/defibrillation therapy is required. Low energy therapy (e.g. antitachycardia pacing) may then be delivered via the sensing/pacing leads to the appropriate location(s). High energy cardioversion/defibrillation pulses may be delivered to the atria via the atrial shocking coils 19 and 20, or to the ventricles via the ventricular shocking coil 18 with several shock vectors possible using the shocking coils and ICD case in various configurations. The ICD detects numerous other types of dysrhythmias within the heart and provides responsive therapy as well. Examples of other dysrhythmias detected by the ICD include bradycardia, supraventricular tachycardia (SVT) and the like.

Figure 2:
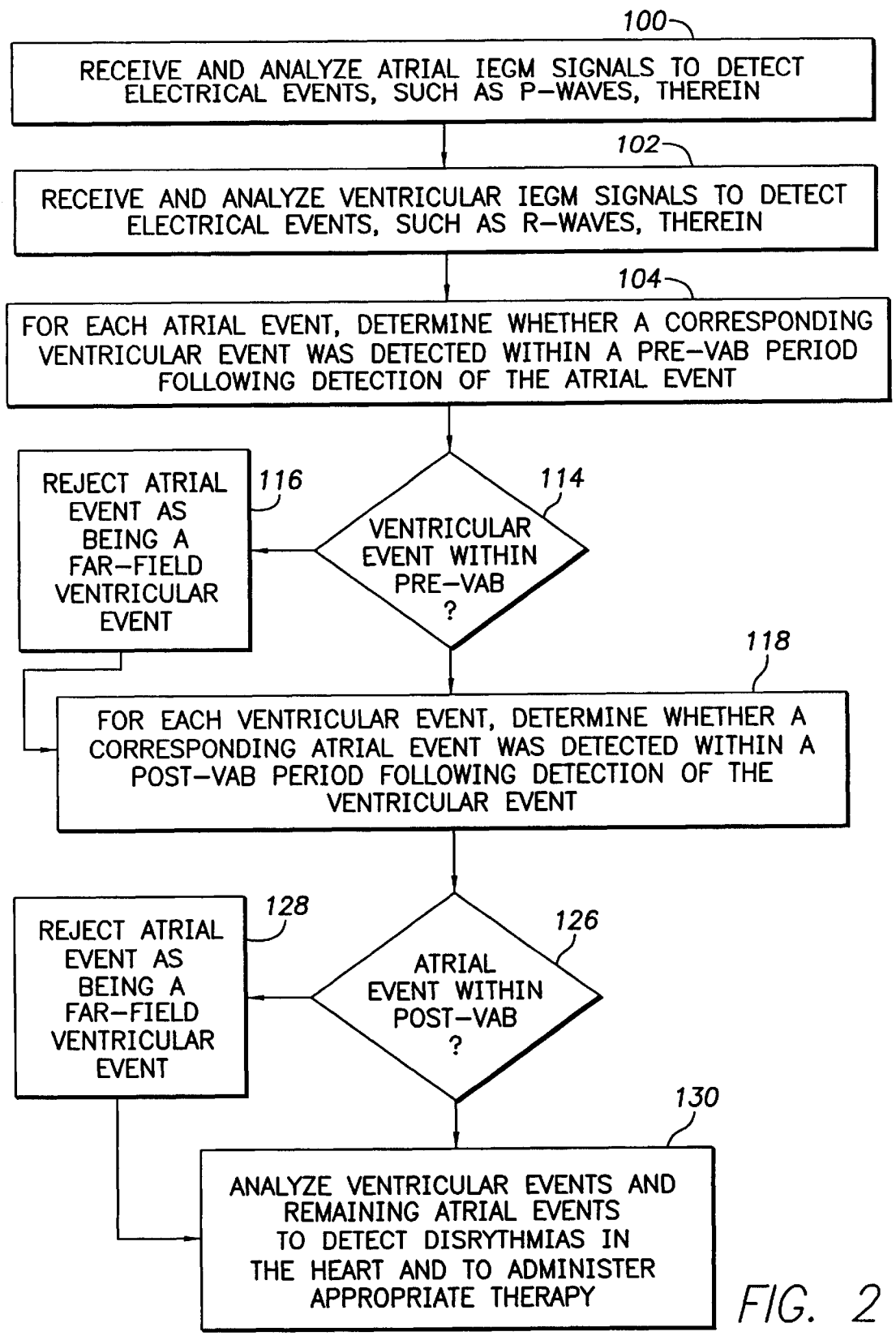
FIG. 2 is a flow chart illustrating a method employed by the ICD of FIG. 1 to distinguish electrical events originating within the atria, such as P-waves, from electrical events not originating in the atria, such as far-field R-waves using both pre-and post-ventricular atrial blanking intervals.
Figure 3:
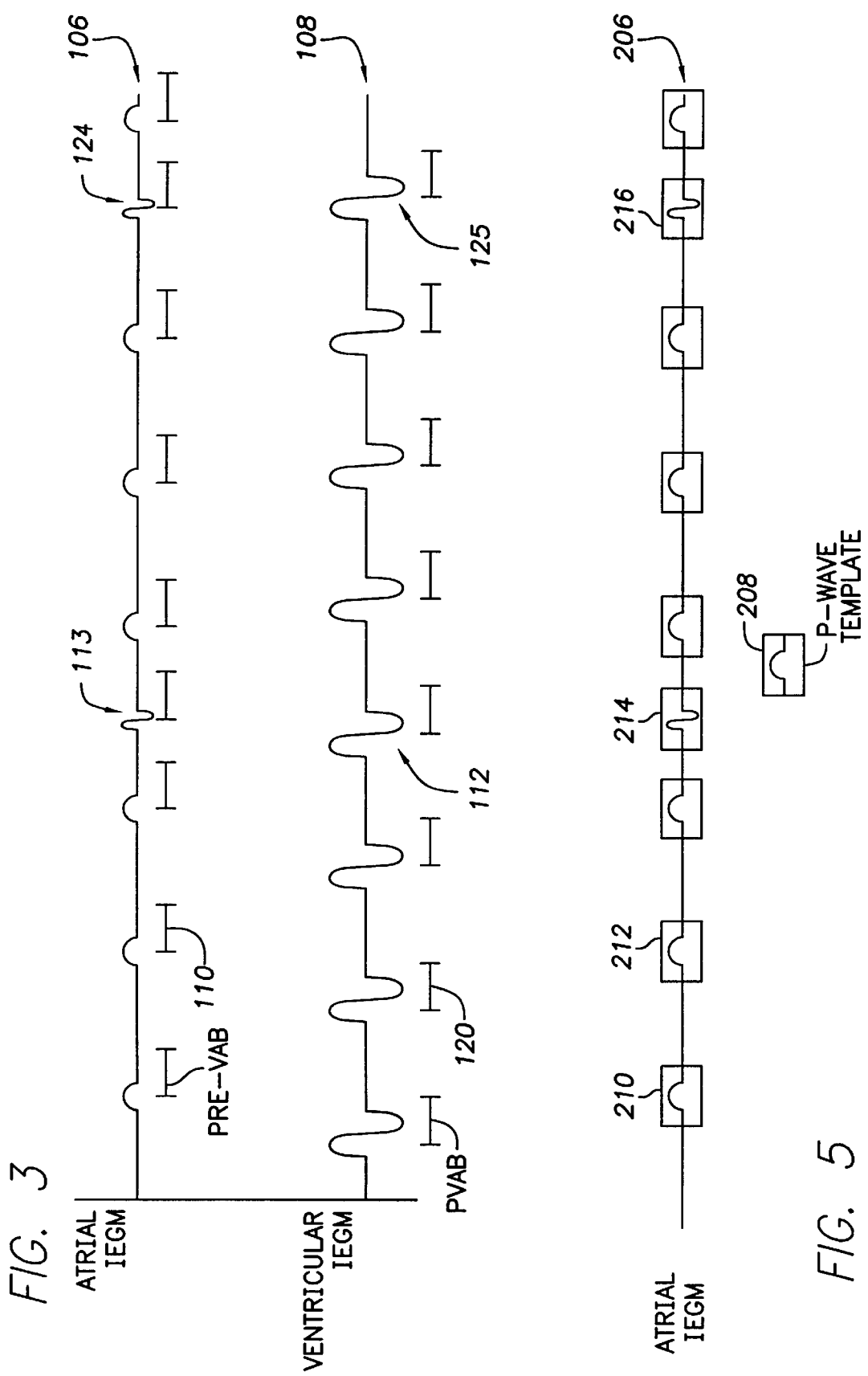
FIG. 3 is a graph illustrating atrial and ventricular IEGM signals processed by the method of FIG. 2 and, in particular, illustrating true and false P-waves.

Many of the functions performed by the ICD of FIG. 1 require accurate detection of P-waves within the atrial IEGM signal. FIGS. 2 and 3 illustrate a first technique for distinguishing P-waves (or other electrical events originating in the atria) from R-waves (or other electrical events not originating in the atria) so that functions performed by the ICD of FIG. 1 which rely on proper detection of atrial events are operate more effectively.

Within FIG. 2, at step 100, the ICD receives and analyzes atrial IEGM signals to detect electrical events represented therein. If the atria are not currently subject to flutter or fibrillation, the detected events may be P-waves. If the atria are subject to flutter or fibrillation such that organized P-waves cannot easily be discerned, the detected events may be voltage threshold crossings or other detectible electrical events. Herein, an electrically detectible event detected within an atrial IEGM is referred to as an $F_A$-wave. Hence, a P-wave is one type of $F_A$-wave. At step 102, the ICD receives and analyzes ventricular IEGM signals to detect electrical events, such as R-waves, represented therein. If the ventricles are not currently subject to flutter or fibrillation, the detected events may be R-waves. If the ventricles are subject to flutter or fibrillation such that organized R-waves cannot easily be discerned, the detected events may be voltage threshold crossings or the like. Herein, an electrically detectible event detected within a ventricular IEGM signal is referred to as an $F_v$-wave. Hence, an R-wave is one type of $F_v$-wave. Steps 100 and 102 are typically performed concurrently. At step 104, for each atrial event that has been detected within the atrial IEGM signal, the ICD determines whether a corresponding ventricular event was detected within the ventricular IEGM signal within a pre-VAB period following detection of the atrial event. In other words, upon detection of a P-wave, the ICD begins tracking a pre-VAB period and determines whether an R-wave is detected within the pre-VAB period.

The pre-VAB interval is illustrated within FIG. 3. Briefly, FIG. 3 illustrates an atrial IEGM signal 106 and a ventricular IEGM signal 108. The atrial IEGM signal includes various events detected therein. Beginning at each event detected within the atrial IEGM, the ICD tracks a pre-VAB period 110 and determines whether a ventricular event is detected within the ventricular IEGM within that time period. If a ventricular event is detected within the pre-VAB time period, then the atrial event is discarded as being a far-field ventricular event. Within FIG. 3, one of the ventricular events (112) is detected within the pre-VAB period of a preceding atrial event (113). Accordingly, atrial event 113 is discarded as being a far-field ventricular event. Note that the far-field ventricular event is actually detected within the atrial IEGM signal before the event is detected within the ventricular IEGM signal. As discussed above, this may occur if the atrial sensing lead is closer to the portion of the ventricle wherein the R-wave originates than the ventricular sensing lead. The duration of the pre-VAB period is preferably a programmable feature of the ICD. In one example, the pre-VAB period is programmable within the range of 0–60 milliseconds.

Referring again to FIG. 2, if a ventricular event is detected within the pre-VAB period, step 114, then the atrial event is discarded as being a far-field ventricular event, step 116. Then, for each ventricular event, the ICD determines at step 118 whether an atrial event is detected within a post-VAB period following detection of the ventricular event. This is also illustrated within FIG. 3 wherein a post-VAB period 120 begins upon detection of each ventricular event detected within the ventricular IEGM signal. One of the atrial events (124) is detected within the post-VAB period of a preceding ventricular event (125). Accordingly, atrial event 124 is discarded as being a far-field ventricular event. Thus, referring again to FIG. 2, if the atrial event is detected within the post-VAB period at step 126, then the atrial event is rejected at step 128 as being a far-field ventricular event. The duration of the post-VAB period is also preferably a programmable parameter of the ICD. In one example, the post-VAB period is programmable within the range of 10–250 milliseconds.

At step 130, the ICD analyzes all ventricular events and any remaining atrial events to detect dysrhythmias, if any, occurring within the heart and to administer appropriate therapy. As noted above, the dysrhythmias may be, for example, bradycardia, tachycardia, atrial flutter, or other dysrhythmias. The appropriate therapy administered by the ICD depends upon the nature of the dysrhythmia and may include, for example, anti-bradycardial pacing, anti-tachycardial pacing, or the administration of atrial or ventricular cardioversion pulses. Some exemplary techniques for administering therapy are provided in the above-referenced U.S. Pat. No. 5,620,471 to Duncan. Note, also, that within step 130 all other functions performed by the ICD which require reliable detection of atrial events are thereby rendered more accurate by properly eliminating all far-field R-waves, or other far-field ventricular events, from the atrial IEGM signal. Thus, for example, ICD functions involving upper rate limit bradycardial functions such as 2:1 block response mode or Wenkebach mode operate more effectively. Details regarding 2:1 block response mode is provided within U.S. Pat. No. 5,601,613 to Florio et al., entitled "Method and Apparatus for Providing Enhanced 2:1 Block Response with Rate-Responsive AV Delay in a Pacemaker", issued Feb. 11, 1997, which is incorporated by reference herein. Details regarding Wenkebach mode are provided in U.S. Pat. No. 5,788,717 to Mann et aL, entitled "Atrial Rate Determination and Atrial Tachycardia Detection in a Dual-Chamber Implantable Pacemaker", issued Aug. 4, 1998, which is incorporated by reference herein. Other functions which benefit from proper discrimination of true atrial events from other events detected within the atrial IEGM signal include mode switching functions and the like. Details regarding mode switching functions are provided in U.S. Pat. No. 5,342,405 to Duncan, entitled "System and Method for Selecting a Mode of Operation of a Dual-Chamber Pacemaker", issued Aug. 30, 1994, which is also incorporated by reference herein. Also, within step 130 the ICD may record the detection of each electrical event in the atrial IEGM signal along with an indication of whether the event was rejected as being a far-field event of the ventricle. The ICD may further record an indication of whether the rejected event was rejected as being within the pre-VAB period or within the post-VAB period.

Figure 4:
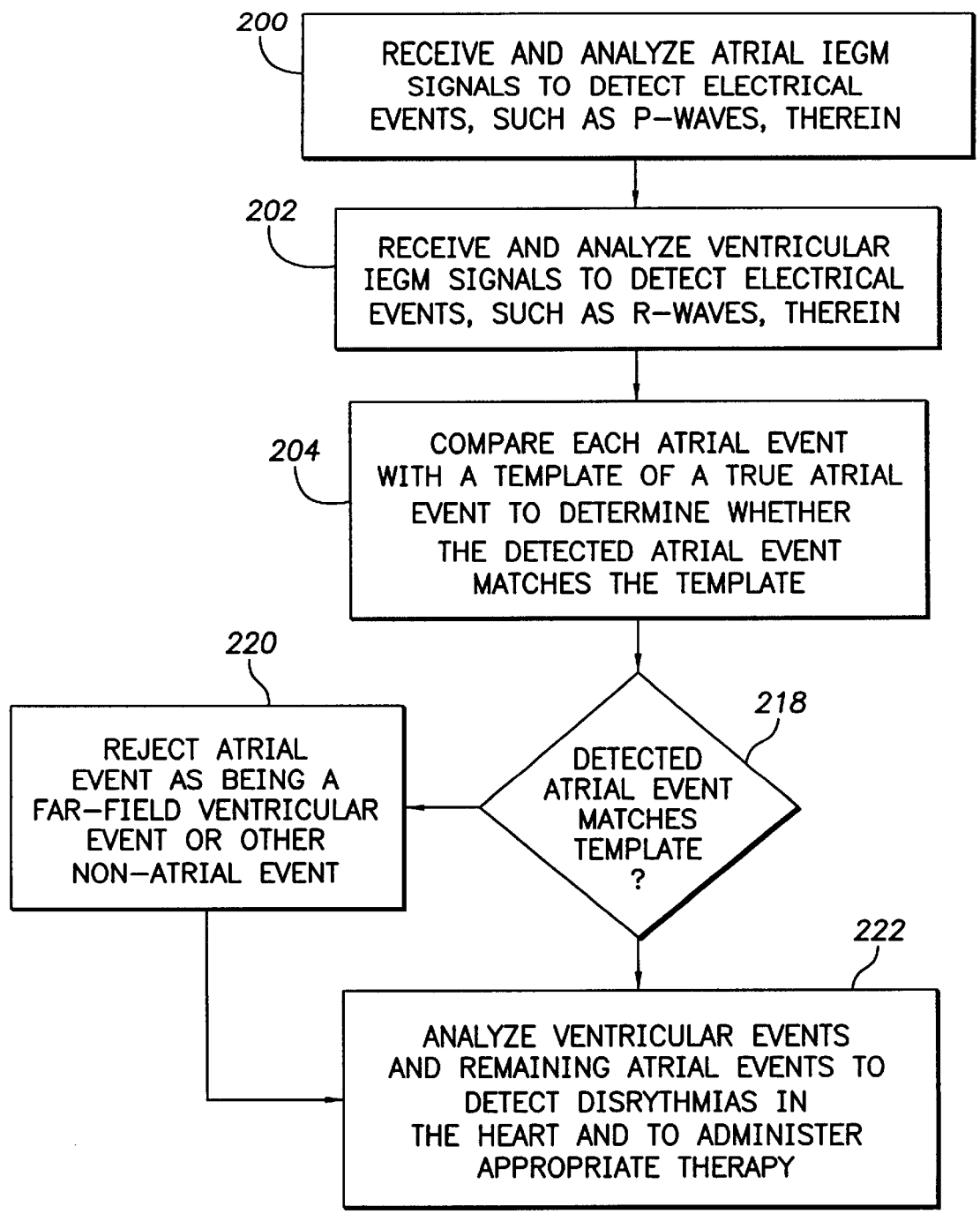
FIG. 4 is a flow chart illustrating a method employed by the ICD of FIG. 1 to distinguish electrical events originating within the atria, such as P-waves, from electrical events not originating in the ventricles, such as far-field R-waves, using templates representative of true atrial events.

With reference to FIGS. 4 and 5, a second technique for discriminating true atrial events from other events will now be described. Beginning at step 200 of FIG. 4, the ICD receives and analyzes atrial IEGM signals to detect electrical events therein. If the atria are not subject to fibrillation of flutter, the atrial events may be P-waves. Otherwise, the atrial events may be other types of $F_A$-waves. In some circumstances, even if the atria are not subject to flutter or fibrillation, it may be appropriate to detect other types of $F_A$-waves besides P-waves. In any case, at step 202 the ICD receives and analyzes ventricular IEGM signals to detect electrical events, such as R-waves, therein. Then, for each atrial event, the ICD compares the atrial event at step 204 with a predetermined template representative of true atrial events to determine whether the detected atrial event matches the template. This is illustrated in FIG. 5.

Briefly, FIG. 5 provides an atrial IEGM signal 206 in which numerous detected events are illustrated. FIG. 5 also illustrates a template 208 representative of a true P-wave. Within step 204 of FIG. 4, the ICD compares each event detected within the atrial IEGM with the template to determine if there is a substantial similarity. Atrial events such as events 210 and 212 substantially match the P-wave template and thereby are deemed to be true P-waves. However, events 214 and 216 do not substantially match the P-wave template and therefore are discarded as not being true P-waves. Indeed, as can be seen within FIG. 5, events 214 and 216 are actually far-field R-waves. Referring again to FIG. 4, if the atrial events do not match the template at step 218, the atrial event is rejected at step 220 as being a far-field ventricular event or other non-atrial event. Otherwise, the atrial event is not rejected. In either case, at step 222 the ICD analyzes the ventricular events and any remaining atrial events to detect dysrhythmias, if any, in the heart and to administer appropriate therapy or to perform any other function requiring accurate identification of atrial events.

The P-waves and far-field R-waves illustrated in FIG. 5 are represented as stylized events for clarity in illustrating the concept of the invention. In practical applications, the atrial IEGM signal is subject to considerable noise. Accordingly, in some implementations, the atrial IEGM signal may be filtered prior to comparison against the template to help prevent noise from interfering with the comparison. Also, the comparison between the detected events and the template need not require an absolute match. Rather, it is sufficient that the detected atrial event correspond to the template to within some predetermined threshold of variation. The exact threshold depends upon the particular characteristics represented by the template and upon the amount of noise in the atrial IEGM signal. The appropriate threshold, in each implementation, may be determined for example by performing routine experimentation using test atrial IEGM signals against stored test templates.

Further with regard to FIG. 5, although the example illustrated therein provides a P-wave template representative of the shape of a true P-wave, alternative templates may be employed which represent other detectable characteristics of true atrial events. For example, the template may represent only the frequency content of true atrial events. If so, the events detected within the atrial IEGM signal are processed to extract the frequency components therein using, for example, a conventional frequency extraction method such as the Fast Fourier Transform (FFT). The frequency components extracted from the atrial IEGM signal are then compared with the frequency components stored in the template. If the frequency components of the atrial IEGM signal substantially match those of the template, a conclusion is drawn that the atrial event is a true atrial event. Numerous other features representative of true atrial events may be alternatively represented within a template for comparison against corresponding features of the atrial IEGM signal. In some implementations, two or more templates representative of different features are employed to provide more reliable rejection of non-atrial events. For example, one template represents the amplitude components of a true atrial event, whereas another template represents the frequency components of a true atrial event.

Also, the specific template used may depend upon the current status of the ICD and upon the current dysrhythmia, if any, detected within the heart. For example, if the ICD has already determined that the heart is subject to flutter, then a template representative of an atrial wave form expected to occur during flutter may be employed. On the other hand, if the ICD has determined that the atria are subject to a tachycardia, then a wave form representative of a tachycardial P-wave may be employed. The shape of the template also may be modulated based upon the current detected atrial rate. As can be appreciated, numerous modifications may be provided to the examples described herein in accordance with the general concept of the invention.

Finally with respect to both FIGS. 3 and 5, the IEGM signals illustrated therein show P-waves and R-waves. Alternatively, other electrical events may be detected. Examples include some predetermined number of consecutive zero voltage crossings or the like.

Although described with respect to examples wherein atrial signals from the left and right atria are merged to yield a single atrial IEGM signal and wherein ventricular signal from the left and right atria are merged to yield a single ventricular IEGM signal, the invention is also applicable to discriminating atrial events from non-atrial events using the separate left and right atrial and ventricular IEGM signals. In one example, the left atrial IEGM is compared with only the left ventricular IEGM using the pre-VAB. Likewise, the right atrial IEGM is compared with only the right ventricular IEGM using the pre-VAB. A P-wave is rejected if either the left or right IEGM comparison identifies the P-wave as being a far-field R-wave. In other implementations, the P-wave is rejected only if both the left and right IEGM comparisons identify the P-wave as being a far-field R-wave. In implementations wherein template matching is employed and multiple atrial IEGM signals are processed, a P-wave is rejected as being a far-field R-wave if the P-wave within any one of the atrial IEGM signals fails to match the template. In other implementations, the P-wave is rejected only if all of the representations of the P-wave within all of the atrial IEGM signals fail to match the template. As can be appreciated, numerous variations are consistent with the general scope of the invention. Aspects of the invention as it pertains to the discrimination of atrial events from ventricular events are also applicable to techniques for determining periods of electrical coherence within the heart for the purposes, for example, of administering cardioversion pulses during periods of coherence. These techniques are described in greater detail in copending U.S. Provisional Patent Application Ser. No. 60/173,341, filed Dec. 28, 1999, entitled "Method and Apparatus for Detecting Natural Electrical Coherence Within the Heart and for Administering Therapy Based Thereon", assigned to the assignee of the present invention, and incorporated by reference herein.

Figure 6:
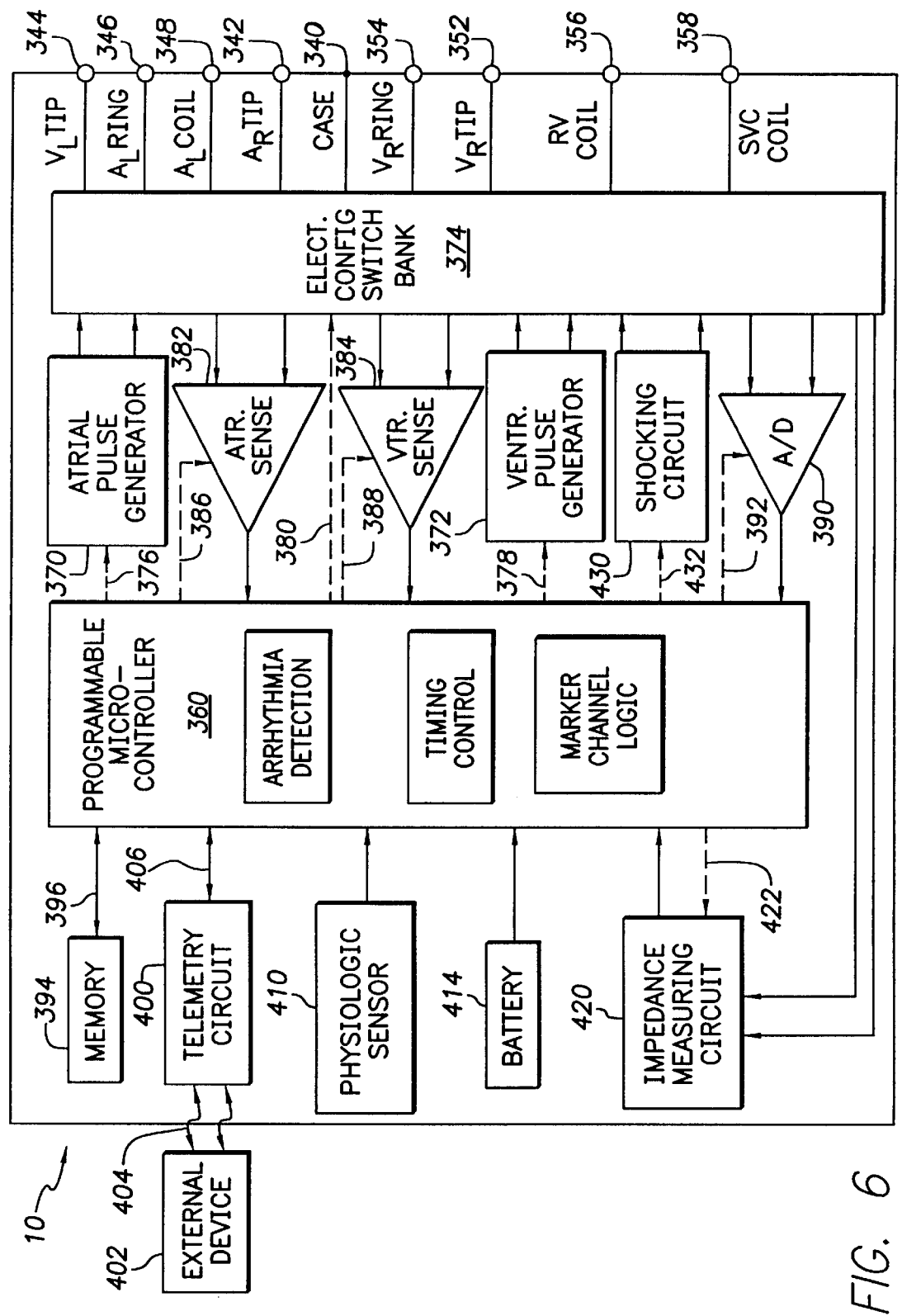
FIG. 6 is a functional block diagram of a dual-chamber implantable stimulation device that may be configured to perform the methods of FIGS. 2–5.

FIG. 6 illustrates internal components of an ICD that configured to perform the method described above in connection with FIGS. 2–5.

The housing 340 for the stimulation device 10, shown schematically in FIG. 6, is often referred to as the "can", "case" or "case electrode" and may be programmably selected to act as the return electrode for all "unipolar" modes. The housing 340 may further be used as a return electrode alone or in combination with one or more of the coil electrodes, 18, 19 or 20, for shocking purposes. The housing 340 further includes a connector (not shown) having a plurality of terminals, 342, 344, 346, 348, 352, 354, 356, and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 22.

To achieve left chamber sensing, pacing and shocking, the connector includes at least a left ventricular tip terminal ($V_L$ TIP) 344, a left atrial ring terminal ($A_L$ RING) 46, and a left atrial shocking terminal ($A_L$ COIL) 348, which are adapted for connection to the left ventricular ring electrode 25, the left atrial electrode 26, and the left atrial coil electrode 19, respectively.

To support right chamber sensing, pacing and shocking, the connector further includes a right ventricular tip terminal ($VR_R$ TIP) 352, a right ventricular ring terminal ($V_R$ RING) 354, a right ventricular shocking terminal (RV COIL) 356, and an SVC shocking terminal (SVC COIL) 358, which are adapted for connection to the right ventricular tip electrode 24, right ventricular ring electrode 25, the RV coil electrode 18, and the SVC coil electrode 20, respectively.

At the core of the stimulation device 10 is a programmable microcontroller 360 which controls the various modes of stimulation therapy and performs, in combination with other units of the ICD, the methods described above in connection with FIGS. 2–5. As is well known in the art, the microcontroller 360 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the present invention. Rather, any suitable microcontroller 360 may be used that carries out the functions described herein. The use of microprocessor-based control circuits for performing timing and data analysis functions is well known in the art. As shown in FIG. 6, an atrial pulse generator 370 and a ventricular pulse generator 372 generate pacing stimulation pulses for delivery by the atrial lead 16 and the ventricular lead 14, respectively, via a switch bank 374. The pulse generators, 370 and 372, are controlled by the microcontroller 360 via appropriate control signals, 376 and 378, respectively, to trigger or inhibit the stimulation pulses. The microcontroller 360 further includes timing circuitry that controls the operation of the stimulation device timing of such stimulation pulses that is well known in the art.

The switch bank 374 includes a plurality of switches for switchably connecting the desired electrodes to the appropriate I/O circuits, thereby providing complete electrode programmability. Accordingly, the switch bank 374, in response to a control signal 380 from the microcontroller 360, determines the polarity of the stimulation pulses (e.g., unipolar or bipolar) by selectively closing the appropriate combination of switches (not shown) as is known in the art.

An atrial sense amplifier 382 and a ventricular sense amplifier 384 are also coupled to the atrial and ventricular leads, 16 and 14, respectively, through the switch bank 374 for detecting the presence of cardiac activity. The switch bank 374 determines the "sensing polarity" of the cardiac signal by selectively closing the appropriate switches, as is also known in the art. In this way, the clinician may program the sensing polarity independent of the stimulation polarity.

Each sense amplifier, 382 and 384, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers 382 and 384 are connected to the microcontroller 360, which, in turn, inhibit the atrial and ventricular pulse generators 370 and 372, respectively, in a demand fashion whenever cardiac activity is sensed in the respective chambers.

For arrhythmia detection is typically performed by the microcontroller 360, in conjunction with the atrial and ventricular sense amplifiers 382 and 384 to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 360 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the atrial and ventricular leads, 16 and 14, through the switch bank 374 to sample cardiac signals across any pair of desired electrodes.

The microcontroller 360 is further coupled to a memory 394 by a suitable data/address bus 396, wherein the programmable operating parameters used by the microcontroller 360 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 328 within each respective tier of therapy.

Advantageously, the operating parameters of the implantable device 10 may be non-invasively programmed into the memory 394 through a telemetry circuit 400 in telemetric communication with an external device 402, such as a programmer, transtelephonic transceiver, or a diagnostic system analyzer. The telemetry circuit 400 is activated by the microcontroller by a control signal 406. The telemetry circuit 400 advantageously allows intracardiac electrograms and status information relating to the operation of the device 10 (as contained in the microcontroller 360 or memory 394) to be sent to the external device 402 through the established communication link 404. In the preferred embodiment, the stimulation device 10 further includes a physiologic sensor 410. Such sensors are commonly called "rate-responsive" sensors. The physiological sensor 410 is used to detect the exercise state of the patient, to which the microcontroller 360 responds by adjusting the rate and AV Delay at which the atrial and ventricular pulse generators 370 and 372 generate stimulation pulses. The type of sensor used is not critical to the present invention and is shown only for completeness.

The stimulation device additionally includes a battery 414, which provides operating power to all of the circuits shown in FIG. 6. For the stimulation device 10, which employs shocking therapy, the battery must be capable of operating at low current drains for long periods of time, and then be capable of providing high-current pulses (for capacitor charging) when the patient requires a shock pulse. The battery 414 must also have a predictable discharge characteristic so that elective replacement time can be detected. Accordingly, the present invention employs lithium/silver vanadium oxide batteries, as is true for most (if not all) such devices to date.

As further shown in FIG. 6, the ICD of the invention may include an impedance measuring circuit 420 which is enabled by the microcontroller 360 by a control signal 422. The impedance measuring circuit 420 is not critical to the present invention and is shown for only completeness.

The ICD detects the occurrence of an arrhythmia, and automatically applies an appropriate electrical shock therapy to the heart aimed at terminating the detected arrhythmia. To this end, the microcontroller 360 further controls a shocking circuit 430 by way of a control signal 432. The shocking circuit 430 generates shocking pulses of low (up to 0.5 joules), moderate (0.5–10 joules), or high energy (11 to 40 joules), as controlled by the microcontroller 360. Such shocking pulses are applied to the patient's heart through at least two shocking electrodes, and as shown in this embodiment, using the RV and SVC coil electrodes 18 and 20, respectively. In alternative embodiments, the housing 340 may act as an active electrode in combination with the RV electrode 18 alone, or as part of a split electrical vector using the SVC coil electrode 20 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Aspects of the invention may be embodied within software running within a programmable processor within the device or may be implemented as hard-wired logic within an application specific integrated circuit (ASIC) or the like.

Accordingly, and as one of skill in the art can appreciate, the present invention can be employed with the microcontroller system described in FIG. 6. What has been described are various techniques for discriminating true atrial events from non-atrial events and for adjusting or administering therapy based thereon. Aspects of the invention are also applicable to discriminating true ventricular events such as R-waves from non-ventricular events such as P-waves. In general, the embodiments described herein are merely illustrative of the invention and should not be construed as limiting the scope of the invention, which is to be interpreted in accordance with the claims that follow.

What is claimed is:

1. A method for discriminating electrical events originating in the atria from electrical events originating with the ventricles of a heart using an implantable medical device receiving signals detected from within an atrium of the heart and receiving signals detected from within a ventricle of the heart, the method comprising the steps of:

detecting an electrical event within the atrium;

detecting an electrical event within the ventricle; and determining whether the electrical event occurring within the ventricle was detected within a predetermined pre-ventricular blanking interval following detection of the electrical event occurring within the atrium and, if so, rejecting the electrical event of the atrium as being a far-field electrical event of the ventricle.

2. The method of claim 1, further comprising the step of:

determining whether the electrical event of the atrium was detected within a predetermined post-ventricular blanking interval following detection of the electrical event of the ventricle and, if so, rejecting the electrical event of the atrium as being a far-field electrical event of the ventricle.

3. The method of claim 1, wherein the electrical event of the atrium is a P-wave.

4. The method of claim 1, wherein the electrical event of the ventricle is an R-wave.

5. The method of claim 1, further comprising the step of: administering therapy based upon the detected events of the ventricles in combination with the detected events of the atrium not rejected as being far-field events of the ventricle.

6. The method of claim 5, wherein the step of administering therapy includes the steps of:

identifying an dysrhythmia, if any, in the heart;

determining therapy to be applied to remedy the dysrhythmia; and applying the therapy to the heart.

7. The method of claim 6, wherein the dysrhythmia is bradycardia, tachycardia, fibrillation or flutter.

8. The method of claim 1, further comprising the step of performing functions based, in part, on the detected events of the atrium not rejected as being far-field events of the ventricle.

9. The method of claim 8, wherein the step of performing functions includes the steps of performing mode switching functions, pre-ventricular contraction detection functions, PV tracking functions, 2:1 blocking functions, and Wenkebach mode functions.

10. A system for discriminating electrical events originating in the atria from electrical events originating with the ventricles of a heart using an implantable medical device receiving signals detected from within an atrium of the heart and receiving signals detected from within a ventricle of the heart, the system comprising:

means for detecting an electrical event occurring within the atrium;

means for detecting an electrical event occurring within the ventricle; and means for determining whether the electrical event occurring within the ventricle was detected within a predetermined pre-ventricular blanking interval following detection of the electrical event occurring within the atrium and, if so, for rejecting the electrical event occurring within the atrium as being a far-field electrical event of the ventricle.

11. The system of claim 10, further comprising:

means for determining whether the electrical event of the atrium was detected within a predetermined post-ventricular blanking interval following detection of the electrical event of the ventricle; and means, responsive to a determination that the electrical event of the atrium was detected within the predetermined post-ventricular blanking interval, for rejecting the electrical event of the atrium as being a far-field electrical event of the ventricle.

12. The system of claim 10, further comprising means for administering therapy based upon the detected events of the ventricles in combination with the detected events of the atrium not rejected as being far-field events of the ventricle.

13. A system for discriminating electrical events originating in the atria from electrical events originating with the ventricles of a heart using an implantable medical device receiving signals detected from within an atrium of the heart and receiving signals detected from within a ventricle of the heart, the system comprising:

an atrial sense amplifier for detecting an electrical event occurring within the atrium;

an ventricular sense amplifier for detecting an electrical event occurring within the ventricle; and a controller for determining whether the electrical event occurring with the ventricle was detected within a predetermined pre-ventricular blanking interval following detection of the electrical event occurring within the atrium and, if so, rejecting the electrical event of the atrium as being a far-field electrical event of the ventricle.

14. The system of claim 13, wherein the controller also determines whether the electrical event of the atrium was detected within a predetermined post-ventricular blanking interval following detection of the electrical event of the ventricle and, if so, rejects the electrical event of the atrium as being a far-field electrical event of the ventricle.

15. The system of claim 13, wherein the controller also generates therapy for applying to the heart based upon the detected events of the ventricles in combination with the detected events of the atrium not rejected as being far-field events of the ventricle.

* * * * *